United States Patent
Khalaj Amineh et al.

(10) Patent No.: US 10,139,371 B2
(45) Date of Patent: *Nov. 27, 2018

(54) CASING DEFECT DETERMINATION USING EDDY CURRENT TECHNIQUES

(71) Applicant: Halliburton Energy Services, Inc., Houston, TX (US)

(72) Inventors: Reza Khalaj Amineh, Houston, TX (US); Luis Emilio San Martin, Houston, TX (US); Burkay Donderici, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 1 day.

This patent is subject to a terminal disclaimer.

(21) Appl. No.: 15/318,039

(22) PCT Filed: Jul. 10, 2015

(86) PCT No.: PCT/US2015/040006

§ 371 (c)(1),
(2) Date: Dec. 12, 2016

(87) PCT Pub. No.: WO2016/007894

PCT Pub. Date: Jan. 14, 2016

(65) Prior Publication Data

US 2017/0138905 A1    May 18, 2017

Related U.S. Application Data

(60) Provisional application No. 62/023,765, filed on Jul. 11, 2014.

(51) Int. Cl.
*G01V 3/00* (2006.01)
*G01N 27/90* (2006.01)
*E21B 47/00* (2012.01)

(52) U.S. Cl.
CPC ......... *G01N 27/90* (2013.01); *E21B 47/0006* (2013.01)

(58) Field of Classification Search
CPC .................. G01N 27/90; E21B 47/0006
(Continued)

(56) References Cited

U.S. PATENT DOCUMENTS

| 4,292,589 A | 9/1981 | Bonner |
| 5,717,169 A | 2/1998 | Liang et al. |

(Continued)

FOREIGN PATENT DOCUMENTS

| WO | 2014035285 A1 | 3/2014 |
| WO | 2016007938 A1 | 1/2016 |

OTHER PUBLICATIONS

Garcia, Javier, et al. "Successful Application of a New Electromagnetic Corrosion Tool for Well Integrity Evaluation in old wells completed with reduced diameter tubular." IPTC 2013: International Petroleum Technology Conference. 2013.

(Continued)

*Primary Examiner* — Reena Aurora
(74) *Attorney, Agent, or Firm* — Scott Richardson; Baker Botts L.L.P.

(57) ABSTRACT

A system comprises one or more electromagnetic coils configured to generate and direct excitation signals toward a plurality of casings in a wellbore and receive response signals based on the excitation signals. The system further comprises one or more processors configured to receive a first response signal from the one or more electromagnetic coils and determine one or more characteristics of a first defect in the plurality of casings using the first response signal and small defect information.

21 Claims, 5 Drawing Sheets

(58) Field of Classification Search
USPC .................................................. 324/238, 333
See application file for complete search history.

(56) References Cited

U.S. PATENT DOCUMENTS

| | | | |
|---|---|---|---|
| 8,076,929 | B2 | 12/2011 | Badoux et al. |
| 9,745,845 | B2* | 8/2017 | San Martin ......... E21B 47/0002 |
| 2006/0202685 | A1 | 9/2006 | Barolak et al. |
| 2009/0195244 | A1 | 8/2009 | Mouget et al. |
| 2015/0338541 | A1* | 11/2015 | Nichols .................... G01V 3/26 |
| | | | 324/338 |

OTHER PUBLICATIONS

Arbuzov, Andrey Alexandrovich. "Memory magnetic imaging defectoscopy." SPE Paper 162054, SPE Russian Oil and Gas Exploration and Production Technical Conference and Exhibition. Society of Petroleum Engineers, 2012.

International Search Report and Written Opinion issued in related PCT Application No. PCT/US2015/040006 dated Sep. 25, 2015, 11 pages.

International Preliminary Report on Patentability issued in related Application No. PCT/US2015/040006, dated Jan. 26, 2017 (10 pages).

Extended European Search Report issued in EP Application No. 15818226.1, dated Dec. 7, 2017, 7 pages.

* cited by examiner

CASING DEFECT DETERMINATION USING EDDY CURRENT TECHNIQUES

CROSS-REFERENCE TO RELATED APPLICATION

The present application is a U.S. National Stage Application of International Application No. PCT/US2015/040006 filed Jul. 10, 2015, which claims priority to U.S. Provisional Patent Application No. 62/023,765 filed Jul. 11, 2014, both of which are incorporated herein by reference in their entirety for all purposes.

BACKGROUND

This disclosure generally relates to wellbore casing evaluation. In particular, this disclosure relates to systems and methods for wellbore casing evaluation using eddy current (EC) techniques.

Hydrocarbons, such as oil and gas, are commonly obtained from wellbores in subterranean formations located onshore or offshore. During operations, the condition of the wellbore casing may deteriorate with one or more defects appearing in the wellbore casing. The defects may be caused by corrosion or other factors, and such defects may make wellbore operations inefficient, may hinder production from the wellbore, or may damage the environment. Current methods of wellbore casing analysis may include casing removal, which may be both expensive and time consuming, particularly in offshore platforms.

BRIEF DESCRIPTION OF THE DRAWINGS

These drawings illustrate certain aspects of certain embodiments of the present disclosure. They should not be used to limit or define the disclosure.

While embodiments of this disclosure have been depicted and described and are defined by reference to example embodiments of the disclosure, such references do not imply a limitation on the disclosure, and no such limitation is to be inferred. The subject matter disclosed is capable of considerable modification, alteration, and equivalents in form and function, as will occur to those skilled in the pertinent art and having the benefit of this disclosure. The depicted and described embodiments of this disclosure are examples only, and not exhaustive of the scope of the disclosure.

DETAILED DESCRIPTION

The present disclosure describes systems and methods for wellbore casing evaluation using eddy current (EC) techniques (e.g., pulsed EC techniques). More particularly, aspects of the present disclosure include the use of time-domain evaluation techniques that may improve the resolution of evaluated defects in wellbore casings by closely approximating the size and shape of the defects using a priori-known small defect information (or minimum-defect information). The small defect information may include information regarding the detected response to analyzing the smallest-measureable defect in a casing using pulsed EC techniques. With a priori knowledge of the response to the smallest defect measureable using pulsed EC techniques, the size and shape of larger defects in a casing may be determined by comparing the response signal associated with the larger defect with combinations of the small defect information. Accordingly, a close approximation of the larger defect may be determined, for example, by comparing various sums of small defect response information with the received EC response information associated with the larger defect. In certain embodiments, the Born approximation may be used in such determinations. The disclosed systems and methods may thus lead to better resolution of defects in wellbore casings, allowing for visibility of smaller features of the defects (e.g. flaws and metal). In addition, larger illuminating sources or sensors can be employed while maintaining sufficient resolutions. This may allow for monitoring of multiple casings with larger outer diameters, for example. Characterization of casings with better resolution also may provide a more precise overall evaluation and ultimately lead to a significant positive impact on the well production process.

To facilitate a better understanding of the present disclosure, the following examples of certain embodiments are given. In no way should the following examples be read to limit, or define, the scope of the disclosure. Embodiments of the present disclosure may be applicable to horizontal, vertical, deviated, multilateral, u-tube connection, intersection, bypass (drill around a mid-depth stuck fish and back into the wellbore below), or otherwise nonlinear wellbores in any type of subterranean formation. Certain embodiments may be applicable, for example, to logging data acquired with wireline, and slickline. Certain embodiments may be applicable to subsea and/or deep sea wellbores. Embodiments described below with respect to one implementation are not intended to be limiting.

Figure 1:
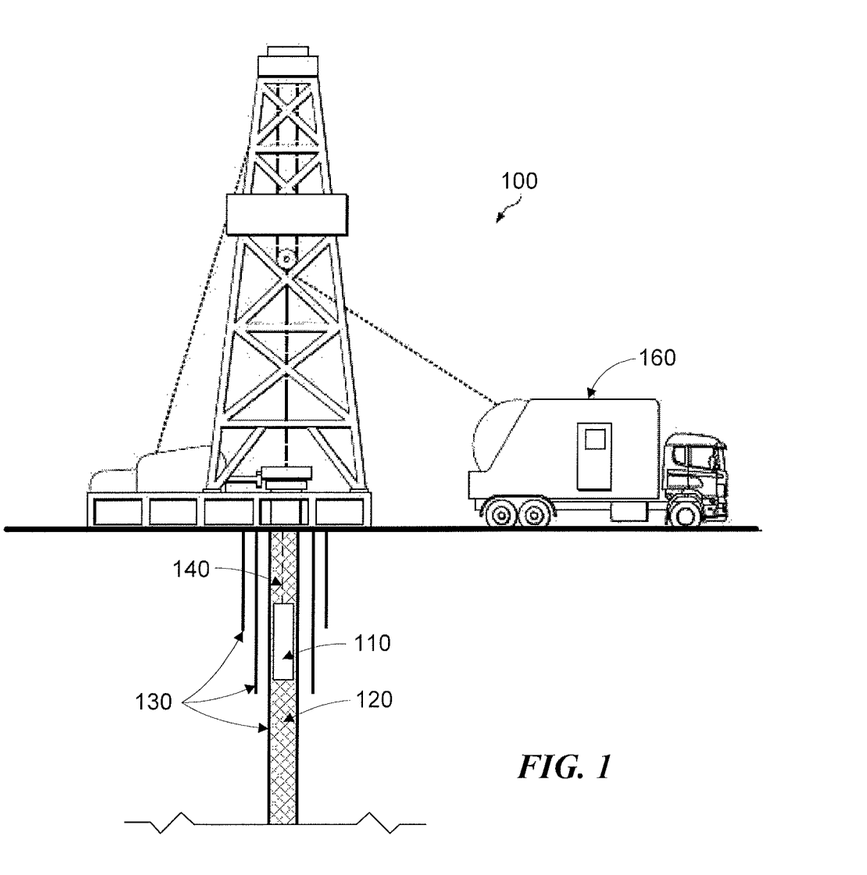
FIG. 1 illustrates an example downhole logging system used in a hydrocarbon drilling environment in accordance with embodiments of the present disclosure.

FIG. 1 illustrates an example downhole logging system 100 used in a hydrocarbon drilling environment in accordance with embodiments of the present disclosure. Operations in a wellbore (e.g., logging or other data collection) may be conducted using downhole inspection tool 110 when some or all of a drill string has been removed from the wellbore. Downhole inspection tool 110 may include one or more logging tools (e.g., casing evaluation tools) that may be suspended into wellbore 120 (which may be formed by multiple casings 130) by cable 140 (e.g., wireline, slickline, or coiled tubing). Downhole inspection tool 110 may be communicatively coupled to cable 140, which may contain conductors for transporting power to downhole inspection tool 110 and signals from logging tools included therein to logging facility 160. However, cable 140 may alternatively lack a conductor, as is often the case using slickline or coiled tubing. Logging facility 160 (shown in FIG. 1 as a truck, although it may be any other structure) may collect measurements from downhole inspection tool 110, and may include computing facilities for controlling, processing, or storing the measurements communicated thereto. The computing facilities may be communicatively coupled to the components of downhole logging system 100 through any suitable means. An example computing facility is described further below with reference to computing system 200 of FIG. 2.

Modifications, additions, or omissions may be made to FIG. 1 without departing from the scope of the present disclosure. For example, FIG. 1 illustrates components of downhole logging system 100 in a particular configuration. However, any suitable configuration of components for logging a wellbore may be used. Furthermore, fewer components or additional components beyond those illustrated may be included in downhole logging system 100 without departing from the scope of the present disclosure.

Figure 2:
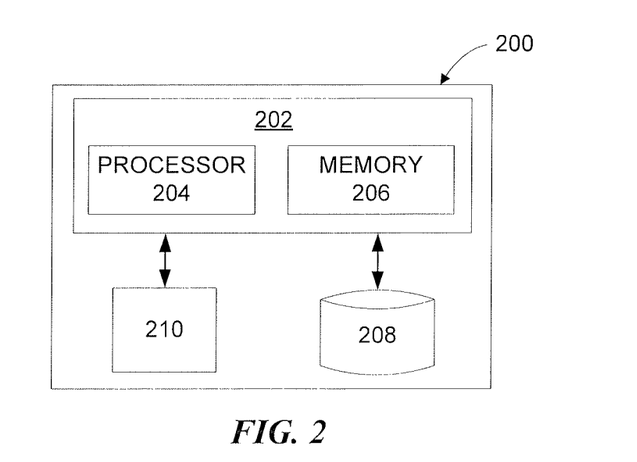
FIG. 2 illustrates a block diagram of an exemplary computing system for use in a downhole logging system in accordance with embodiments of the present disclosure.

FIG. 2 illustrates a block diagram of an exemplary computing system 200 for use in a downhole logging system in accordance with embodiments of the present disclosure. Computing system 200 or components thereof can be located at the surface (e.g., in logging facility 160), downhole (e.g., in downhole inspection tool 110), or some combination of both locations (e.g., certain components may be disposed at the surface while certain other components may be disposed downhole, with the surface components being communicatively coupled to the downhole components). Computing system 200 may be configured to generate excitation signals in one or more electromagnetic coils, and analyze the associated response signals received to determine whether defects exist in wellbore casings, in accordance with the teachings of the present disclosure. For example, computing system 200 may be configured to perform the steps of the methods described below with respect to FIG. 7.

Computing system 200 may include casing evaluation module 202, which includes any suitable components. For example, in some embodiments, casing evaluation module 202 may include a processor 204 communicatively coupled to a memory 206. Processor 204 may include, for example a microprocessor, microcontroller, digital signal processor (DSP), application specific integrated circuit (ASIC), or any other digital or analog circuitry configured to interpret and/or execute program instructions and/or process data. Processor 204 may be configured to interpret and/or execute program instructions or other data retrieved and stored in memory 206. Program instructions or other data may constitute portions of software 208 for carrying out one or more methods described herein. Memory 206 may include any system, device, or apparatus configured to hold and/or house one or more memory modules; for example, memory 206 may include read-only memory, random access memory, solid state memory, or disk-based memory. Each memory module may include any system, device or apparatus configured to retain program instructions and/or data for a period of time (e.g., computer-readable non-transitory media). For example, instructions from software 208 may be retrieved and stored in memory 206 for execution by processor 204. Casing evaluation module 202 may be communicatively coupled to one or more displays 210 (e.g., located in logging facilities 160 of FIG. 1) such that information processed by casing evaluation module 202 may be conveyed to operators of the downhole logging system. For example, casing evaluation module 202 may convey results of defect evaluation methods of the present disclosure to display 210 for viewing by an operator of downhole inspection tool 110 of FIG. 1.

Modifications, additions, or omissions may be made to FIG. 2 without departing from the scope of the present disclosure. For example, FIG. 2 shows a particular configuration of components of computing system 200. However, any suitable configurations of components may be used. For example, components of computing system 200 may be implemented either as physical or logical components. Furthermore, in some embodiments, functionality associated with components of computing system 200 may be implemented in special purpose circuits or components. In other embodiments, functionality associated with components of computing system 200 may be implemented in configurable general purpose circuit or components. For example, components of computing system 200 may be implemented by configured computer program instructions.

Figure 3:
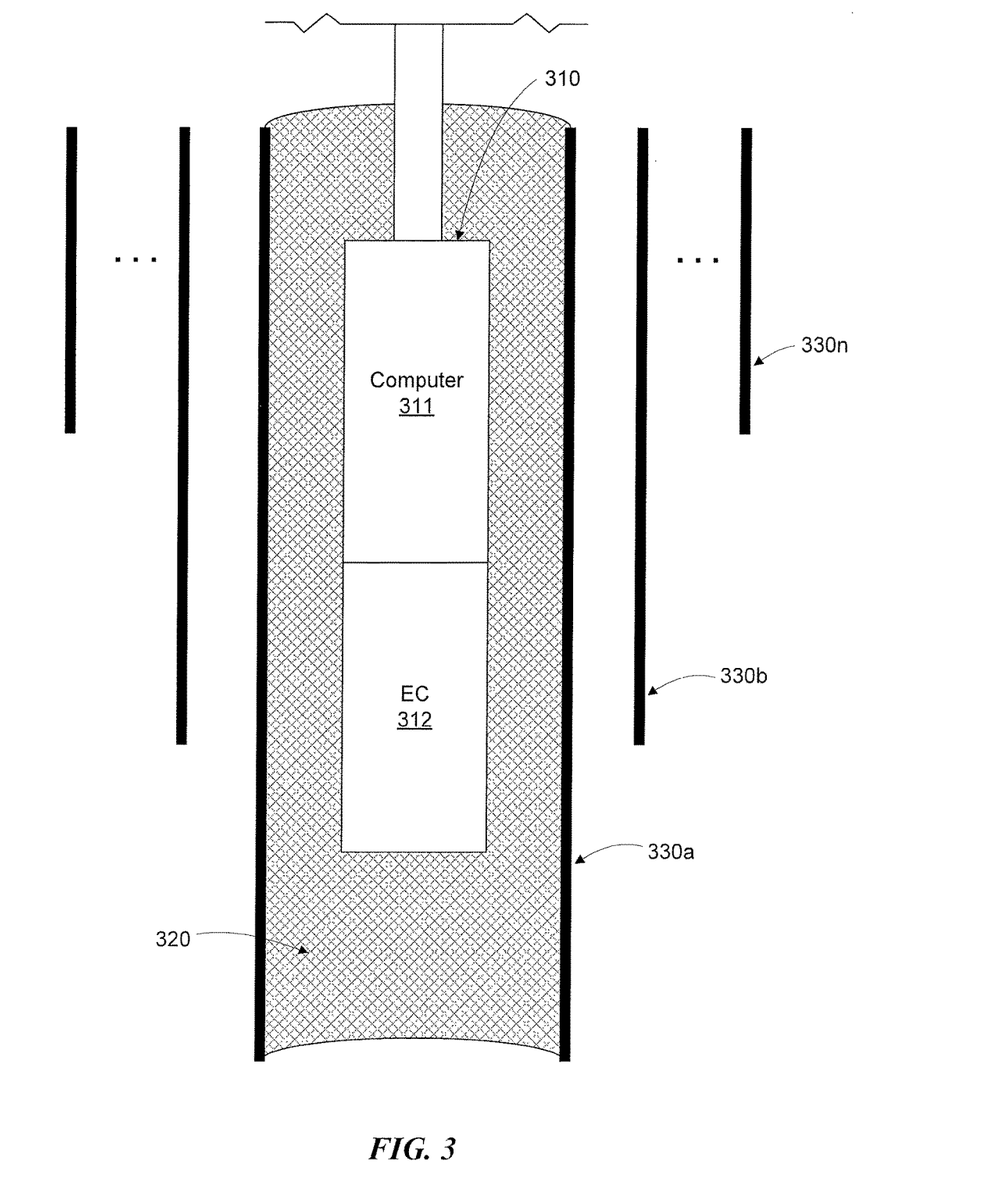
FIG. 3 illustrates a block diagram of an example casing evaluation tool in accordance with embodiments of the present disclosure.

FIG. 3 illustrates a block diagram of an example casing evaluation tool 310 in accordance with embodiments of the present disclosure. More particularly, FIG. 3 depicts a casing evaluation tool 310 that traverses a wellbore 320 comprising a plurality of concentric casings 330. Casing evaluation tool 310 may be a portion of a wireline system (e.g., downhole inspection tool 110 of FIG. 1), and may be configured to measure or provide information associated with casings 330 of wellbore 320. For example, casing evaluation tool may measure or provide estimates of the thickness of each casing 330, the degree of concentricity of casings 330, and/or other parameters associated with casings 330. Casing evaluation tool 310 comprises a computer 311 that may include, for example, a module for communication (e.g., to communicate measurements to a drilling operator uphole), a processor, memory, a battery, or any other suitable components. In some embodiments, computer 311 may comprise components similar to computing system 200 of FIG. 2.

Casing evaluation tool 310 further comprises eddy current (EC) sensor 312, which may each include any suitable hardware and/or software for performing pulsed eddy current wellbore casing evaluation techniques (as described further below). For instance, EC sensor 312 may include transmitter and receiver coils and excitation/data acquisition electronics to implement frequency-domain or time-domain (based on the pulsed eddy current) EC measurements as described below. In particular embodiments of the present disclosure, EC techniques may be employed for inspection of multiple casings (i.e., some or all of casings 330) using EC sensor 312.

Modifications, additions, or omissions may be made to FIG. 3 without departing from the scope of the present disclosure. For example, FIG. 3 shows a particular configuration of components of casing evaluation tool 310. However, any suitable configuration or combination of components may be used. For example, casing evaluation tool 310 may include multiple EC sensors 312. As another example, casing evaluation tool 310 may further include additional sensors for measuring downhole characteristics, such as temperature or pressure.

Figure 4A:
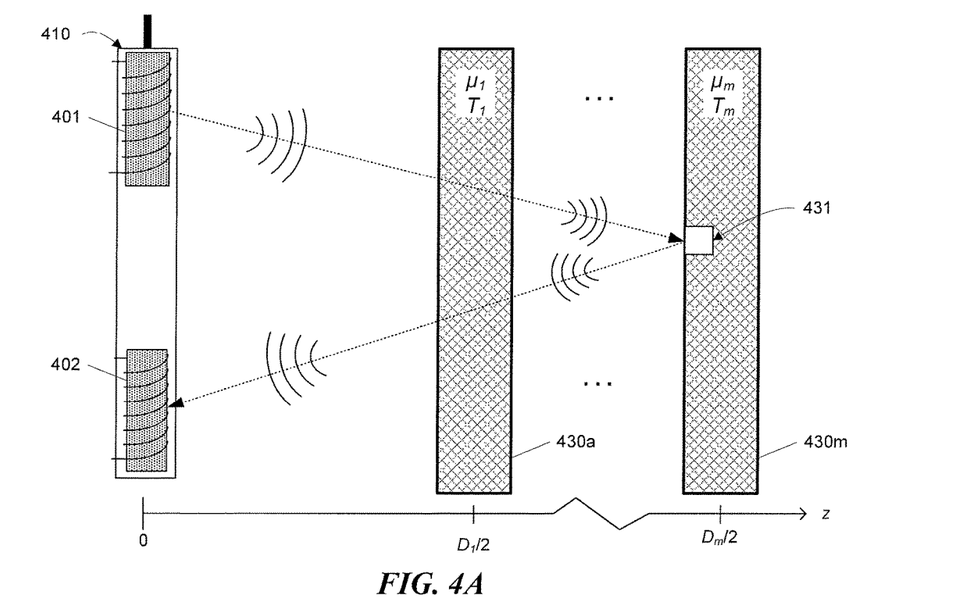
FIGS. 4A-4B illustrate an example method for evaluating the response of casing defects in accordance with embodiments of the present disclosure.
Figure 4B:
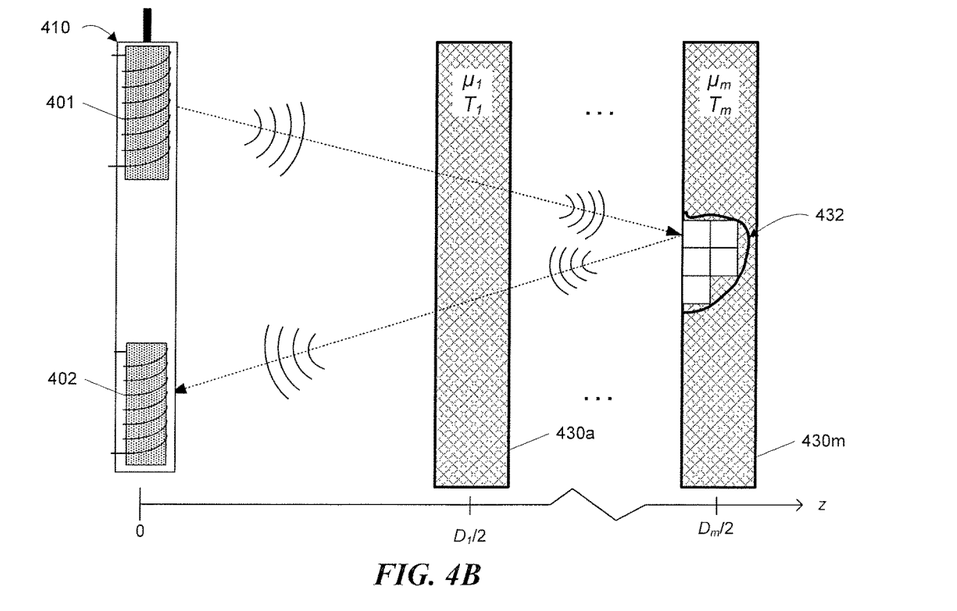

FIGS. 4A-4B illustrate an example method for evaluating the response of casing defects in accordance with embodiments of the present disclosure. In particular, FIGS. 4A-4B illustrate a casing evaluation tool 410 comprising an excitation source 401 configured to generate pulsed EC excitation signals (electromagnetic waves) and direct them toward defects 431 and 432 in casings 430, and a receiver 402 configured to sense response signals (electromagnetic waves) generated in response to the excitation signals transmitted by excitation source 401. Excitation source 401 may include any suitable hardware for generating the pulsed EC signals, such as one or more electromagnetic coils. Similarly, receiver 402 may include any suitable hardware for receiving the response signals to the transmitted pulsed EC signals from excitation source 401, such as one or more electromagnetic coils.

In performing EC casing evaluation techniques, a transmitter coil (e.g., excitation source 401) may emit primary electromagnetic fields (which may be transient in nature), causing eddy currents to be produced in casings of the wellbore (e.g., casings 330 in FIG. 3). These eddy currents may then produce secondary electromagnetic fields that may be sensed by receiver coils (e.g., receiver 402). The acquired data can be then employed to perform evaluation on multiple casings of a wellbore, such as concentric casings. $D_N$ may represent the outer diameter of the N-th casing in the wellbore, $\mu_N$ may represent the permeability of the N-th casing, and $T_N$ may represent the thickness of the N-th casing.

In particular embodiments, a two-dimensional model may be used to determine the size and/or shape of the defects in wellbore casings. FIG. 4A depicts the previously discussed small defect, defect 431, which may represent the smallest defect in the casing that may be detected and/or measured using pulsed EC techniques. If the small defect appears in the m-th casing as shown in FIG. 4A, it may be approximated with a delta function at the radial distance of $D_m/2$ (i.e. $(z, D_m/2)$, where z is the axial position and $D_m/2$ is the radial position). The time-domain response measured by a generic pulsed eddy current sensor at axial position z is thus denoted by $h(z, t, D_m/2)$.

The time-domain response received from measuring the small defect using EC techniques may then be stored as small defect information. In some embodiments, the response (and thus the small defect information) may be calibrated such that it includes the response only from the small defect and not other information caused by other elements of the wellbore (e.g. from other casings, other tools in the downhole inspection tool, or the formation itself). This calibration may be performed, in certain embodiments, by recording the response over the z-axis twice—once with the presence of the defect and once without the defect—and then subtracting the two responses.

Using the determined and stored small defect information, the response of any arbitrary defect (such as defect 432 in FIG. 4B) may then be approximated through discretization into a finite number of small defects as shown in FIG. 4B. The function representing the arbitrary defect may be expressed as the sum of the small defects as shown below in Equation (1):

$$x(z,d) \approx \Sigma_{i=1}^{N} \delta(z+z_l, D_m/2+D_l) \qquad (1)$$

where $z_l$ and $D_l$ are the offsets from the z-axis's origin and $D_m/2$, respectively, and N is the number of small defects that compose the arbitrary defect. If the thickness of the pipe is small compared to the skin depth (e.g., wavelength of the wave propagated toward the defect), or if the defect is small enough that the variation of the small defect signal response with $D_l$ is negligible, then the calibrated response r due to the metal loss function $x(z, d)$ in the m-th casing as shown in FIG. 4B can be written in terms of the small defect response $h(z, t, D_m/2)$ as shown below in Equation (2):

$$r(z,t) = \Sigma_{i=1}^{N} h(z+z_l, t, D_m/2) \qquad (2)$$

Equation (2) therefore provides an approximate and fast forward two-dimensional model that may accurately predict the response due to any arbitrary-shaped defect in a wellbore casing, provided that the response due to a small defect is a priori known. It will be understood that the size of the small defect used for defect estimation purposes may be different for deeper pipes.

It will be understood that the measureable size of the small defect in deeper pipes (i.e., those further away from the sensor) will be larger than that for those closer to the sensor. In particular embodiments, a known small defect response for a defect in a closer casing may be determined by modeling the known small defect response to the casings that are further away.

It will also be understood that two-dimensional forward model described above may provide an estimated measurement of a defect before the average volumetric metal loss has been approximated with an equivalent azimuthally symmetrical metal loss. Thus, there may be a trade-off between the azimuthal extent of the defect and depth of the defect. However, in embodiments with azimuthal sensors employed, the two-dimensional forward modeling approach can be extended to three-dimensions. In such embodiments, Equation (2) may be extended to account for the azimuthal variations as shown below in Equation (3):

$$r(z,\phi,t) \approx \Sigma_{i=1}^{N} h(z+z_l, \phi+\phi_l, t, D_m/2) \qquad (3)$$

where $h(z, \phi, t, D_m/2)$ is the response to small defect at z=0 and $\phi$=0.

In embodiments based on the Born approximation, approximations of defect characteristics may be more valid when the small defects used are very small. Moreover, the accuracy and resolution of the technique may depend on the measurement of the small defect signal response. In addition, the size of the small defect may dictate the resolution of the evaluation system (i.e., how accurately the system may evaluate defects). The defect for which the small defect signal response is measured may therefore represent the smallest defect that can be evaluated by the system, in particular embodiments. In certain embodiments, the variation of the small defect signal response over radial distance and the casing's thickness may also be taken into account. In some embodiments, the small defect signal response can be measured over the radial distance within the casing, and this variation can be included in the image reconstruction process.

In particular embodiments, the acquired response may be compared with the response computed by the forward model described above, with iterative numerical optimization operations being performed to determine the difference between the measured defect and the possible combinations of the small defect information. Intermediate estimates for the defect shape may be determined using the embodiments described above during the optimization process. The iterative numerical optimization may be performed in real time, through the comparison with response signals for particular defect shapes stored in a library or database, or through any suitable combination of the two. In particular embodiments, during the optimization routine, the estimate for the defect shape may be iteratively updated until the difference between the measured response and the computed responses (either from real time predication or from the library) falls below a desired threshold.

In certain embodiments, effects due to the presence of sensor housing, pad structure, mutual coupling between sensors, mud and cement, or any other effects may be corrected by using a priori information on such parameters. In some embodiments, these effects may be additive, so they may be removed using proper calibration schemes. Multiplicative (scaling) portions of the effects may be removed in the process of calibration to an existing log.

Modifications, additions, or omissions may be made to FIGS. 4A-4B without departing from the scope of the present disclosure. For example, FIGS. 4A-4B show a particular configuration of components for measuring defects in wellbore casings. However, any suitable configuration or combination of components may be used. For example, casing evaluation tool 410 may include additional excitation sources 401 and receivers 402 in addition to those illustrated.

Figure 5:
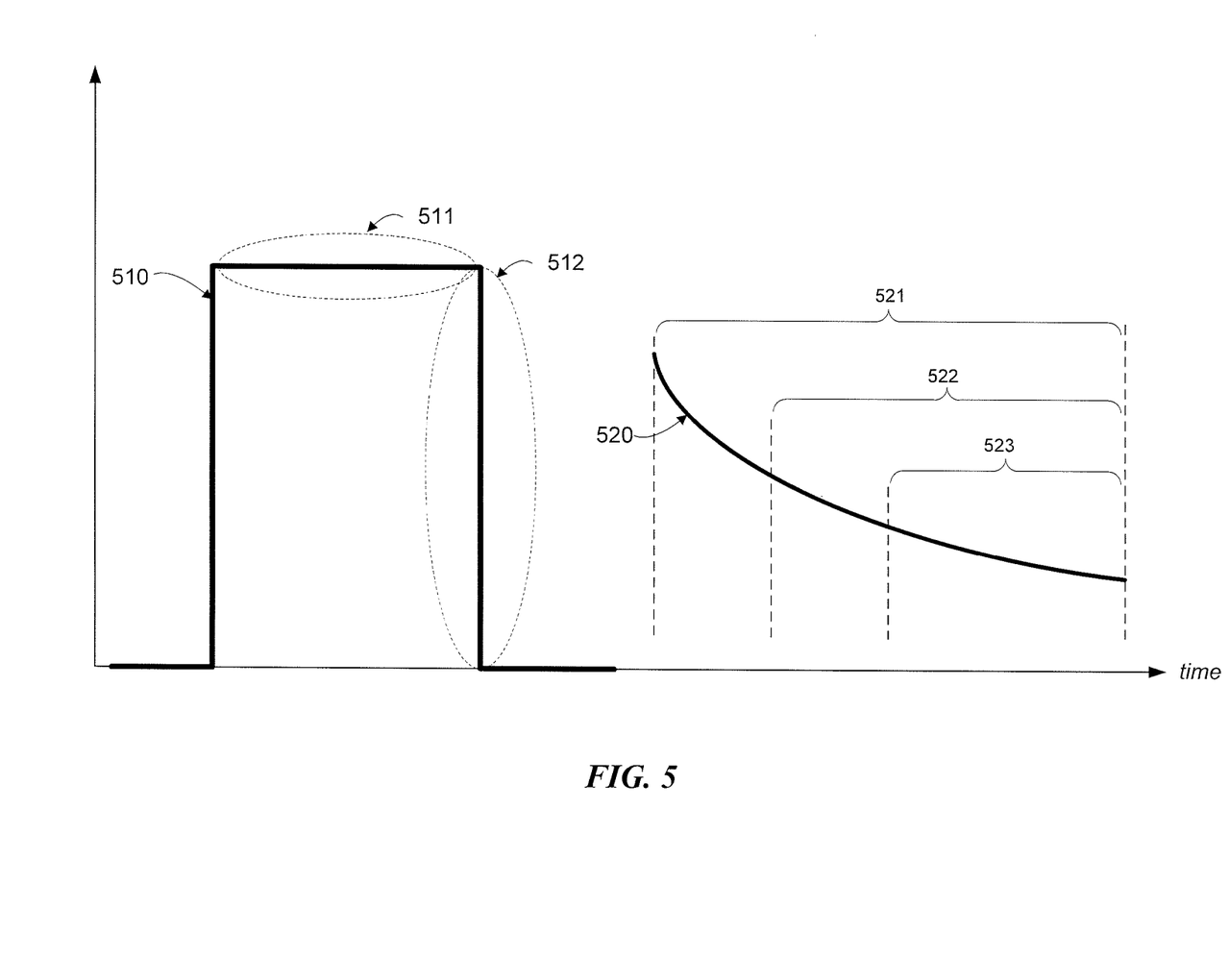
FIG. 5 illustrates an example excitation signal and associated response signal for casing evaluation tools, in accordance with embodiments of the present disclosure.

FIG. 5 illustrates an example excitation signal 510 and associated response signal 520 for casing evaluation tools, in accordance with embodiments of the present disclosure. Excitation signal 510 includes a silent region 611 and an exciting edge 612. Response signal 520 may be representative of a response signal for use in embodiments with multiple concentric pipes for evaluation. When acquiring data for such embodiments using pulsed EC techniques in the time domain, defects on the inner casings appear in the response signal 520 at earlier times while defects on the outer casings appear at later times in the response signal 520 at longer decay times. It may therefore be possible to first estimate the defects of the inner most casings and then, by having these values, estimate the defects of the outer most casings. This can be performed by dividing the decay response of the sensor into regions (as shown by regions 521-523 in FIG. 5) such that the m-th sub-region is affected the most by the m-th casing. By properly processing the values of the decay response during these sub-regions, the defects of multiple casings can be estimated.

It will be understood that the imaging results for embodiments of the present disclosure may be improved by acquiring data with multiple sensors. When employing multiple sensors, the forward modeling approach described above may be performed for each sensor separately first. Then, the measured responses from the other sensors may be combined in a single inversion algorithm to estimate the defects. For this purpose, the small defect signal responses may be known a priori for each individual sensor. In certain embodiments, the data obtained from smaller or shorter sensors may be used to estimate the defects in the inner-most pipes. The estimated values for the inner casing may be used together with data obtained from larger or longer sensors to estimate the defects on the outer-most casings.

In particular embodiments, the small defect signal response may be pre-recorded by measuring small defects or other small holes for a number of casings with variable permeability, thickness, and outer diameters. In some embodiments, this information can be obtained from forward models (analytical or numerical models) through simulations. The size of the measured small defect may be small enough such that the Born approximation holds for a number of them composing the arbitrary defect, while also being large enough to provide measureable response in the evaluation system for a larger size of transmitter and receiver and/or larger dimensions/properties of the casings.

It will be understood that the permeability of the casings of the wellbore will be known a priori in embodiments of the present disclosure. This allows for using the previously recorded small defect responses in the library corresponding to such permeability values. When acquiring data in the time domain, permeability values for outer casings affect the response at longer decay times. The estimation of permeabilities of the individual pipes may be performed, in some embodiments, by dividing the decay response of the sensor into regions (as shown by regions 521-523 in FIG. 5) such that the m-th sub-region is affected the most by the m-th casing. Then, by properly processing the values of the decay response at these sub-regions, the permeability of the casings can be estimated.

Figure 6:
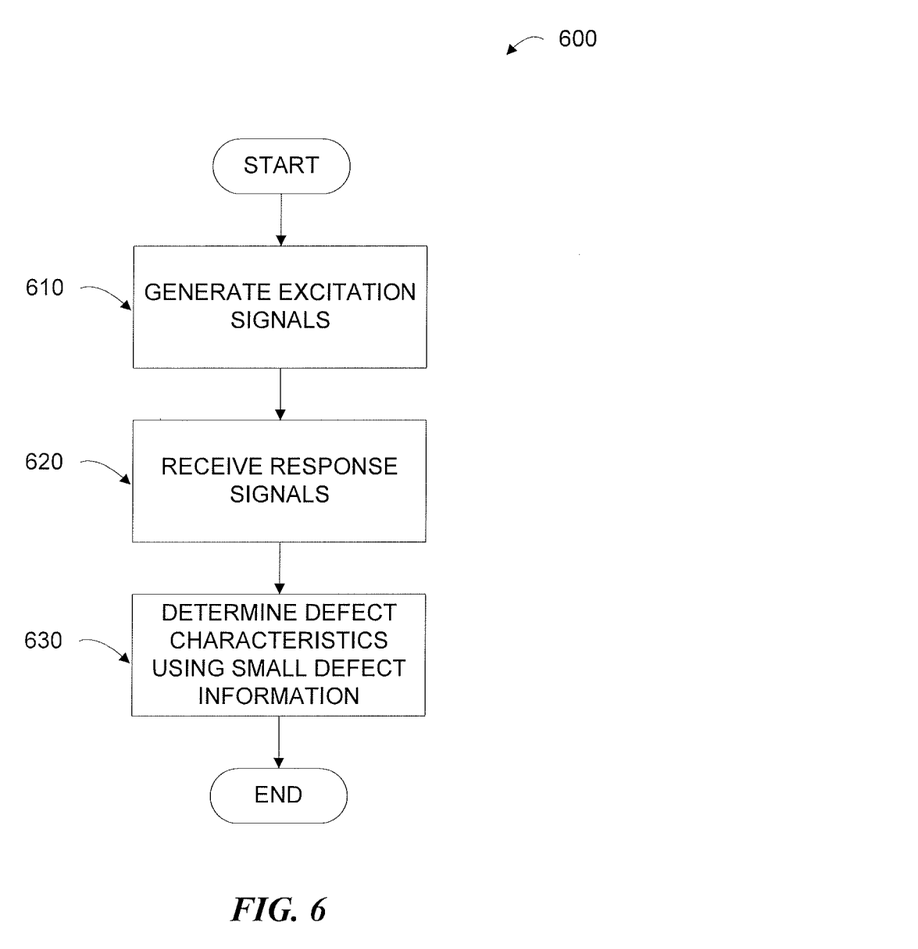
FIG. 6 illustrates an example method for evaluating multiple casings of a wellbore in accordance with embodiments of the present disclosure.

FIG. 6 illustrates an example method 600 for evaluating multiple casings of a wellbore in accordance with embodiments of the present disclosure. The method begins at step 610, where excitation signals are generated. The excitation signals may be generated using one or more electromagnetic coils, which may be configured to direct electromagnetic waves toward a first defect of a plurality of casings in a wellbore. For example, generation of an excitation signal for EC techniques may include generating transient electromagnetic fields using a coil (e.g., transmitter 401 of FIGS. 4A-4B), as described above.

At step 620, response signals are received. The response signals may be received in response to generation of the excitation signals in step 610. For example, response signals to EC excitation signals may include electromagnetic waves generated by eddy currents in the one or more casings caused by the excitation signal (i.e., transient electromagnetic fields generated using a coil), as discussed above. Such response signals may be received by a coil, such as receiver 402 in FIGS. 4A-4B or any other suitable coil or antenna.

At step 630, one or more characteristics of defects in the one or more wellbore casings are determined, which may be done using response signals received at step 620 and small defect information. The small defect information may include information indicating a magnitude of a received response signal associated with a small defect in a casing, wherein the small defect is of a size below which the magnitude of the response signal will be zero. As described above, in certain embodiments, determining one or more characteristics of defects may include comparing one or more combinations of the small defect information to the first response signal. By determining a combination of small defects that most closely represents the response signal received at step 620, the one or more characteristics of defects in the casings may be determined. Characteristics of the defects may include a size of the defect, a shape of the defect, or any suitable combination thereof In certain embodiments, the small defect information may be determined using a response signal received in response to directing electromagnetic waves toward a small defect in a wellbore casing, wherein the defect is of a size below which the magnitude of the response signal will be zero. Furthermore, in some embodiments, the small defect information may be determined using another response signal received in response to directing electromagnetic waves toward a casing without defects. The small defect information may thus be determined by subtracting the two signals (i.e., subtracting the no-defect response signal from the response signal returned from the small defect).

In certain embodiments, determining the one or more characteristics of the defects may be based on portions of the response signal. For instance, referring to FIG. 6, characteristics of defects in an inner-most casing of concentric casings may be based on region 521 of response signal 520, while characteristics of defects in an outer casing of concentric casings may be based on region 522 or 523 of response signal 520.

Modifications, additions, or omissions may be made to method 600 without departing from the scope of the present disclosure. For example, the order of the steps may be performed in a different manner than that described and some steps may be performed at the same time. Additionally, each individual step may include additional steps without departing from the scope of the present disclosure.

To provide illustrations of one or more embodiments of the present disclosure, the following examples are provided.

In one embodiment, a system comprises one or more electromagnetic coils configured to generate and direct excitation signals toward a plurality of casings in a wellbore and receive response signals based on the excitation signals.

The system further comprises one or more processors configured to receive a first response signal from the one or more electromagnetic coils and determine one or more characteristics of a first defect in the plurality of casings using the first response signal and small defect information.

In one or more aspects of the disclosed system, determining one or more characteristics of the first defect using the first response signal and small defect information comprises comparing one or more combinations of the small defect information to the first response signal.

In one or more aspects of the disclosed system, the small defect information comprises information, for each particular casing of the plurality of casings, indicating a magnitude of a received second response signal associated with a defect in the particular casing of the plurality of casings, the defect being of a size below which the magnitude of the second response signal will be zero.

In one or more aspects of the disclosed system, determining one or more characteristics of the first defect is based on a portion of the first response signal.

In one or more aspects of the disclosed system, the one or more characteristics of the first defect comprises a size of the first defect, a shape of the first defect, or a combination thereof.

In one or more aspects of the disclosed system, the small defect information is determined using a second response signal received from the one or more electromagnetic coils in response to excitation signals directed toward a second defect in the plurality of casings.

In one or more aspects of the disclosed system, the small defect information is determined using a third response signal received in response to excitation signals directed toward a casing of the plurality of casings without defects.

In another embodiment, a method comprises generating and directing an excitation signal toward a plurality of casings in a wellbore using one or more electromagnetic coils, receiving a first response signal from the one or more electromagnetic coils based on the excitation signal, and determining one or more characteristics of a first defect in the plurality of casings using the first response signal and small defect information.

In one or more aspects of the disclosed method, determining one or more characteristics of the first defect using the first response signal and small defect information comprises comparing one or more combinations of the small defect information to the first response signal.

In one or more aspects of the disclosed method, the small defect information comprises information, for each particular casing of the plurality of casings, indicating a magnitude of a received second response signal associated with a defect in the particular casing of the plurality of casings, the defect being of a size below which the magnitude of the second response signal will be zero.

In one or more aspects of the disclosed method, determining one or more characteristics of the first defect is based on a portion of the first response signal.

In one or more aspects of the disclosed method, the one or more characteristics of the first defect comprises a size of the first defect, a shape of the first defect, or a combination thereof.

In one or more aspects of the disclosed method, the small defect information is determined using a second response signal received from the one or more electromagnetic coils in response to excitation signals directed toward a second defect in the plurality of casings.

In one or more aspects of the disclosed method, the small defect information is determined using a third response signal received in response to excitation signals directed toward a casing of the plurality of casings without defects.

In another embodiment, a computer-readable medium compries instructions that are configured, when executed by a processor, to receive a first response signal from one or more electromagnetic coils, and determine one or more characteristics of a first defect in a plurality of casings using the first response signal and small defect information.

In one or more aspects of the disclosed computer-readable medium, the instructions configured to determine one or more characteristics of the first defect using the first response signal and small defect information are further configured to compare one or more combinations of the small defect information to the first response signal.

In one or more aspects of the disclosed computer-readable medium, the small defect information comprises information, for each particular casing of the plurality of casings, indicating a magnitude of a received second response signal associated with a defect in the particular casing of the plurality of casings, the defect being of a size below which the magnitude of the second response signal will be zero.

In one or more aspects of the disclosed computer-readable medium, determining one or more characteristics of the first defect is based on a portion of the first response signal.

In one or more aspects of the disclosed computer-readable medium, the one or more characteristics of the first defect comprises a size of the first defect, a shape of the first defect, or a combination thereof.

In one or more aspects of the disclosed computer-readable medium, the small defect information is determined using a second response signal received from the one or more electromagnetic coils in response to excitation signals directed toward a second defect in the plurality of casings.

In one or more aspects of the disclosed computer-readable medium, the small defect information is determined using a third response signal received in response to excitation signals directed toward a casing of the plurality of casings without defects.

The terms "couple" or "couples" as used herein are intended to mean either an indirect or a direct connection. Thus, if a first device couples to a second device, that connection may be through a direct connection, or through an indirect electrical or mechanical connection via other devices and connections. The term "uphole" as used herein means along the drill string or the hole from the distal end towards the surface, and "downhole" as used herein means along the drill string or the hole from the surface towards the distal end.

For the purposes of this disclosure, computer-readable media may include any instrumentality or aggregation of instrumentalities that may retain data and/or instructions for a period of time. Computer-readable media may include, for example, without limitation, storage media such as a direct access storage device (e.g., a hard disk drive or floppy disk drive), a sequential access storage device (e.g., a tape disk drive), compact disk, CD-ROM, DVD, RAM, ROM, electrically erasable programmable read-only memory ("EEPROM"), and/or flash memory; as well as communications media such as wires.

The present disclosure is well adapted to attain the ends and advantages mentioned, as well as those that are inherent therein. The particular embodiments disclosed herein are illustrative only, as the present disclosure may be modified and practiced in different but equivalent manners apparent to those skilled in the art having the benefit of the teachings herein. In the interest of clarity, not all features of an actual implementation may be described in this specification. It will of course be appreciated that in the development of any actual embodiment, numerous implementation-specific decisions may be made to achieve the specific implementation goals, which may vary from one implementation to another. Moreover, it will be appreciated that such a development effort might be complex and time-consuming, but would nevertheless be a routine undertaking for those of ordinary skill in the art having the benefit of the present disclosure.

What is claimed is:

1. A system for characterizing a casing, comprising:
an excitation source of a casing evaluation tool, wherein the excitation source comprises one or more transmitter electromagnetic coils configured to:
generate and direct a plurality of excitation signals toward a plurality of casings in a wellbore;
a receiver of the casing evaluation tool, wherein the receiver comprises one or more receiver electromagnetic coils configured to:
receive a plurality of response signals based on the plurality of excitation signals; and
one or more processors configured to:
receive the plurality of received response signals;
determine a small defect information for each of the plurality of received response signals based on a time-domain response associated with each of the plurality of received response signals; and
determine one or more characteristics of a first defect in the plurality of casings by summing the small defect information for each of the plurality of received response signals, wherein the determining the one or more characteristics comprises using a forward model.

2. The system of claim 1, wherein the determining the one or more characteristics of the first defect comprises comparing one or more combinations of the small defect information to a first response signal of the plurality of received response signals.

3. The system of claim 1, wherein the small defect information comprises information, for each particular casing of the plurality of casings, indicating a magnitude of a received second response signal of the plurality of received response signals associated with a defect in the particular casing of the plurality of casings, the defect being of a size below which the magnitude of the second response signal will be zero.

4. The system of claim 1, wherein the determining the one or more characteristics of the first defect is based on a portion of a first response signal of the plurality of received response signals.

5. The system of claim 1, wherein the one or more characteristics of the first defect comprises a size of the first defect, a shape of the first defect, or a combination thereof.

6. The system of claim 1, further comprising:
wherein the one or more transmitter electromagnetic coils are further configured to generate and direct a second excitation signal toward the plurality of casings in the wellbore;
wherein the one or more receiver electromagnetic coils are further configured to receive a second response signal based on the second excitation signal; and
determining a second small defect information for a second response signal received from the one or more receiver electromagnetic coils in response to the second excitation signal directed toward a second defect in the plurality of casings.

7. The system of claim 6, wherein at least one of the small defect information is determined using a third response signal received in response to excitation signals directed toward a casing of the plurality of casings without defects.

8. A method for characterizing a casing, comprising:
generating and directing a plurality of excitation signals toward a plurality of casings in a wellbore using one or more transmitter electromagnetic coils of a casing evaluation tool;
receiving at one or more receivers of the casing evaluation tool a plurality of response signals from the one or more transmitter electromagnetic coils based on the plurality of excitation signals;
determining a small defect information for each of the plurality of received response signals based on a time-domain response associated with each of the plurality of received response signals; and
determining one or more characteristics of a first defect in the plurality of casings by summing small defect information for each of the plurality of received response signals, wherein the determining the one or more characteristics comprises using a forward model.

9. The method of claim 8, wherein the determining the one or more characteristics of the first defect comprises comparing one or more combinations of the small defect information to a first response signal of the plurality of received response signals.

10. The method of claim 8, wherein the small defect information comprises information, for each particular casing of the plurality of casings, indicating a magnitude of a received second response signal of the plurality of received response signals associated with a defect in the particular casing of the plurality of casings, the defect being of a size below which the magnitude of the second response signal will be zero.

11. The method of claim 8, wherein the determining the one or more characteristics of the first defect is based on a portion of a first response signal of the plurality of received response signals.

12. The method of claim 8, wherein the one or more characteristics of the first defect comprises a size of the first defect, a shape of the first defect, or a combination thereof.

13. The method of claim 8, further comprising:
generating and directing a second excitation signal toward the plurality of casings in the wellbore;
receiving a second response signal based on the second excitation signal; and determining a second small defect information for the second response signal received in response a second excitation signal directed toward a second defect in the plurality of casings.

14. The method of claim 13, wherein at least one of the small defect information is determined using a third response signal received in response to excitation signals directed toward a casing of the plurality of casings without defects.

15. A non-transitory computer-readable medium comprising instructions for characterizing a casing, the instructions configured, when executed by a processor, to:
receive a plurality of response signals from one or more receiver electromagnetic coils of a casing evaluation tool, wherein the plurality of response signals are based on a plurality of excitation signals generated by one or more transmitter electromagnetic coils of the casing evaluation tool and directed toward a plurality of casings in a wellbore;
determine a small defect information for each of the plurality of received response signals based on a time-domain response associated with each of the plurality of received response signals; and determine one or more characteristics of a first defect in a plurality of casings by summing small defect information for each of the plurality of received response signals, wherein the determining the one or more characteristics comprises using a forward model.

16. The non-transitory computer-readable medium of claim 15, wherein the determining the one or more characteristics of the first defect comprises comparing one or more combinations of the small defect information to a first response signal of the plurality of received response signals.

17. The non-transitory computer-readable medium of claim 15, wherein the small defect information comprises information, for each particular casing of the plurality of casings, indicating a magnitude of a received second response signal of the plurality of received response signals associated with a defect in the particular casing of the plurality of casings, the defect being of a size below which the magnitude of the second response signal will be zero.

18. The non-transitory computer-readable medium of claim 15, wherein the determining the one or more characteristics of the first defect is based on a portion of a first response signal of the plurality of received response signals.

19. The non-transitory computer-readable medium of claim 15, wherein the one or more characteristics of the first defect comprises a size of the first defect, a shape of the first defect, or a combination thereof.

20. The non-transitory computer-readable medium of claim 15, wherein the instructions for characterizing the casing are further configured, when executed by the processor, to:

generate and direct a second excitation signal toward the plurality of casings in the wellbore;

receive a second response signal based on the second excitation signal; and determine a second small defect information for the second response signal received in response to a second excitation signal directed toward a second defect in the plurality of casings.

21. The non-transitory computer-readable medium of claim 20, wherein at least one of the small defect information is determined using a third response signal received in response to excitation signals directed toward a casing of the plurality of casings without defects.

* * * * *